(12) United States Patent
Palu' et al.

(10) Patent No.: US 6,812,255 B2
(45) Date of Patent: Nov. 2, 2004

(54) USE OF ALOE-EMODIN IN THE TREATMENT OF NEUROECTODERMAL TUMORS

(75) Inventors: Giorgio Palu', Montegrotto Terme (IT); Modesto Carli, Padua (IT); Teresa Pecere, Padua (IT)

(73) Assignee: Universita Degli Studi Di Padova, Padua (IT)

( * ) Notice: Subject to any disclaimer, the term of this patent is extended or adjusted under 35 U.S.C. 154(b) by 85 days.

(21) Appl. No.: 10/306,448

(22) Filed: Nov. 27, 2002

(65) Prior Publication Data

US 2004/0102526 A1 May 27, 2004

(51) Int. Cl.⁷ .............................................. A61K 31/12
(52) U.S. Cl. ..................................................... 514/680
(58) Field of Search ......................................... 514/680

(56) References Cited

PUBLICATIONS

Pecere et al., Cancer Research, vol. 60, No. 11, Jun. 1, 2000, pp 2800–2804.*

* cited by examiner

Primary Examiner—Theodore J. Criares
(74) Attorney, Agent, or Firm—Joseph A. Mahoney; Mayor, Brown, Rowe & Maw LLP

(57) ABSTRACT

The invention relates to the use of anti-cancer drug of a natural compound of vegetal origin, known as aloe-emodin (AE). Indeed, said compound has proved to have a specific biological activity of inhibition on the growth of neuroectodermal tumors, without evident toxic effects. The compound, according to the present invention, has also proved to be cell-specific and it does not show any inhibition on the growth of other cell types such as, for instance, fibroblasts. This pharmacological profile, i.e., tumor-targeting and absence of toxicity, makes said compound particularly advantageous in the treatment of neuroectodermal tumors. Pharmaceutical compositions containing said pharmacological agent can therefore be usefully used in the treatment of the foresaid pathologies.

12 Claims, 6 Drawing Sheets

USE OF ALOE-EMODIN IN THE TREATMENT OF NEUROECTODERMAL TUMORS

FIELD OF THE INVENTION

The present invention relates to a compound known as aloe-emodin (AE) as an active agent for the preparation of pharmaceutical compositions for the treatment of neuroectodermal tumors.

PRIOR ART

It is known that the therapeutic strategies used at present in the treatment of neoplastic pathologies essentially aim at eliminating all malignant cells both on the primary and metastatic sites. To this purpose different therapeutic modalities can be used, from surgery to radiotherapy for tumors which are localized, to chemotherapy for local or distant diseases, to endocrine therapy for hormone-dependent tumors, to immunotherapy up to thermotherapy. All these therapeutic modalities can be used singularly or can also be combined one with the other, according to the type of neoplastic cells and to the stage of the pathology, in order to obtain an effective therapy of eradication of neoplasia.

Chemotherapy is certainly one of the most common therapeutic approaches, both alone and combined with the aforesaid therapeutic modalities. An ideal chemotherapy agent should be selective for the tumoral cells without inducing any relevant adverse effects on normal cells or toxic effects of systemic type; nevertheless, in spite of the long and complex research aiming at finding anti-cancer agent of this kind, up to now no compound, used singularly and combined with other agents, has proved to have a satisfactory therapeutic index, i.e. the effectiveness ratio on the tumoral cells versus absence of cytotoxic effects on non-malignant cells. Several anti-tumor agents are knows and in use, and there are highly different mechanisms causing their cytotoxicity towards tumoral cells. The first agents to be used were alkylating drugs, such as nitrogen mustard, followed by anti-metabolic drugs, folate antagonists such as methotrexate, or purine antagonists such as 6-mercaptopurine, or pirimidine antagonists such as 5-fluorouracil, substances of vegetal origin blocking cell mitosis such as vincristine and vinblastine, and podophyllotoxins, antibiotics such as mitomycin, adriamycin and bleomycin, nitrosoureas, platinum coordination compounds and more recently the so-called biologic response modifiers such as α-interferon and an enzyme such as asparaginase. All these drugs, alone or in combination, are broadly used for several tumoral pathologies from tumors localized in specific organs to disseminated tumors. In the case of neuroectodermal tumors, such as for instance neuroblastoma, primitive peripheral neuroectodermic tumor (pPNET), Ewing's sarcoma, melanoma, microcytoma etc., the chemotherapy agents normally used, though not specific, can be for instance vincristine and vinblastine, platinum coordination compounds and others suitable to this purpose.

Despite the recognized effectiveness of many among these compounds, none of them has nevertheless proved to have the aforesaid ideal profile, and in several cases a certain resistance, also multiple, of tumoral cells towards these agents can even be observed, though toxic effects on other cells do not disappear.

Therefore, with the aim of developing novel anticancer drugs characterized by selective targeting and low toxicity for dividing normal host tissues, the inventors have focused their attention on natural compounds, which have been traditionally used for centuries to treat a wide and various range of highly heterogeneous pathologies and which are characterized in that they have no relevant toxic effect, studying in particular their cytotoxicity towards tumoral cells of human origin, which are not usually used in screenings to verify the potential anti-tumoral effect of known and new compounds.

SUMMARY OF THE INVENTION

After these researches the inventors have now found that a natural substance of vegetal origin, aloe-emodin, surprisingly has a powerful cytotoxic activity, both in vitro and in vivo, against cells of neuroectodermal tumors, without showing a similar cytotoxic activity for dividing normal host tissues.

Aim of the present invention is therefore the use of aloe-emodin for the preparation of pharmaceutical compositions which can be used in the treatment of neuroectodermal tumors.

Aloe-emodin can act as chemotherapy agent inducing a selective cytotoxicity towards those cells through an apoptotic mechanism.

DETAILED DESCRIPTION OF THE INVENTION

The characteristics and advantages of the present invention can be better understood from the following detailed description.

The compound here discussed, i.e. aloe-emodin, can be found in vacuolar juices of the epidermic cells of leaves of various species of Aloe, but also in other plants such as senna and rhubarb, from which it was isolated in free or glycosylated form at the beginning of past century. Till now this compound was used as cathartic.

From the structural point of view it is an hydroxyanthraquinone having in its free form the formula 1,8-dihydroxy-3-hydroxymethyl-9.10-anthracenedione.

The activity of aloe-emodin (AE) as an anti-tumor drug with a specific selective activity against neuroectodermal tumors has been studied in vitro on human tumoral cells and in vivo in mice with a severe combined immunodeficiency (SCID). Furthermore the general toxic effects of AE has been studied on Swiss mice.

In Vitro Bioassays

In vitro cytotoxicity assays have been carried out on different tumoral cell lines both of neuroectodermal tumors and other human malignant cells from epithelial and blood-derived tumors, as well as human hemopoietic progenitors and normal fibroblasts, so as to verify the cytotoxic activity and the specificity of said effect of the compound:

tumors of neuroectodermic origin: neuroblastoma (IMR-32, IMR-5, AF8, SJ-N-KP), pPNET (TC32), Ewing's sarcoma (TC106), melanoma (Mel 23);

tumors of different origin: T-cell leukemia (CEM) and T-cell leukemia vinblastine-resistant (CEM VBL), colon adenocarcinoma (LoVo 109) and colon adenocarcinoma doxorubicin-resistant (LoVo DX), cervix epithelioid carcinoma (HeLa);

normal cells: human lung fibroblasts (MRC5).

Figure 1A:
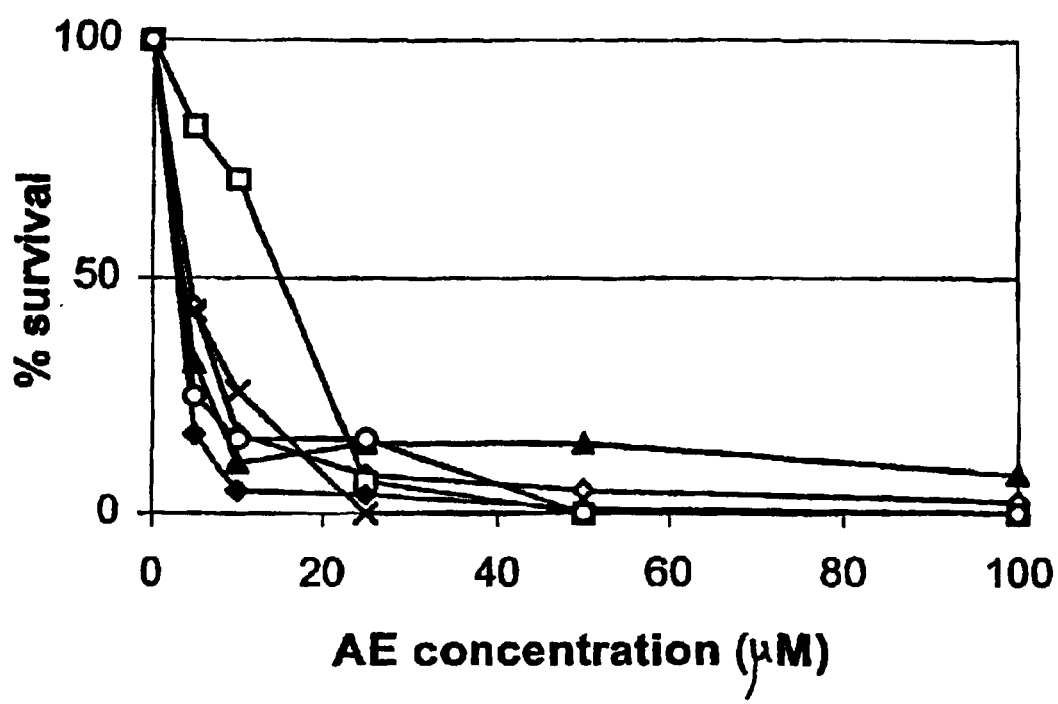
FIG. 1A illustrates AE cytotoxicity dose-response on neuroectodermal tumor cell lines: IMR5 ◇, IMR32 □, AF8 ▲, SJ-N-KP ◆, TC32 x, TC106 ○, Mel23 ● and FIG. 1B on tumoral cells of different origin LoVo 109 ◇, LoVo DX ■, CEM ◆, CEM VBL x, HeLa ○ and on normal human lung fibroblasts MRC5 ●.
Figure 1B:
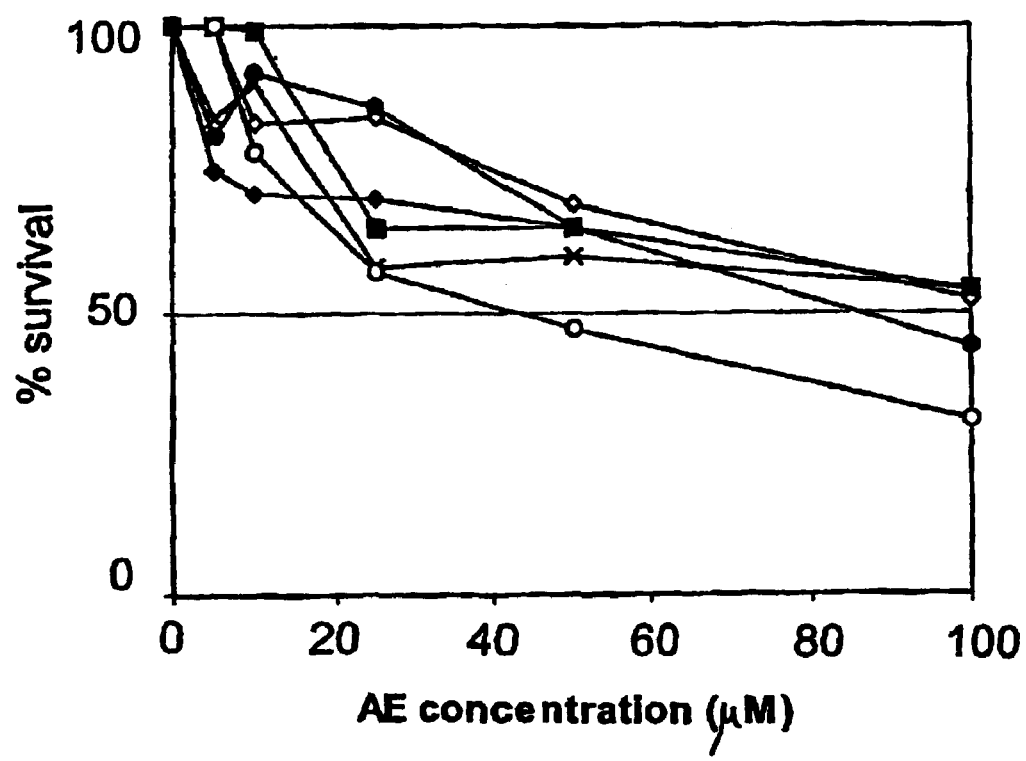
FIG. 1C illustrates the percentage of colony growth of neuroblastoma cells (SJ-N-KP ■) and CFU-GM obtained from bone marrow (BM ▦) of healthy donors and from cord blood (CB □) samples incubated with different concentrations of AE after 14 days.

The cells, in exponentially growing phase in complete medium, are exposed to graduated doses from 0 to 100 $\mu$M of aloe-emodin (AE), over 72 hours. The obtained data indicate ED50 values (half-maximal effective doses) varying from 1 to 13 $\mu$M (for neuroblastoma and Ewing's sarcoma, respectively) and values varying from 40 to 100 $\mu$M (for fibroblasts and acute lymphocytic leukemia lines, respectively). FIG. 1A shows the results obtained on neuroectodermal tumor cells as % of cell survival (IMR5 ◇, IMR32 □, AF8 ▲, SJ-N-KP ♦, TC32 x, TC106 ○, Mel23 ●) and FIG. 1B shows the results as % of cell survival on tumoral cells of different origin and normal cells (LoVo 109 ◇, LoVo DX ■, CEM ♦, CEM VBL x, HeLa ○ and MRC5 ●).

Figure 1C:
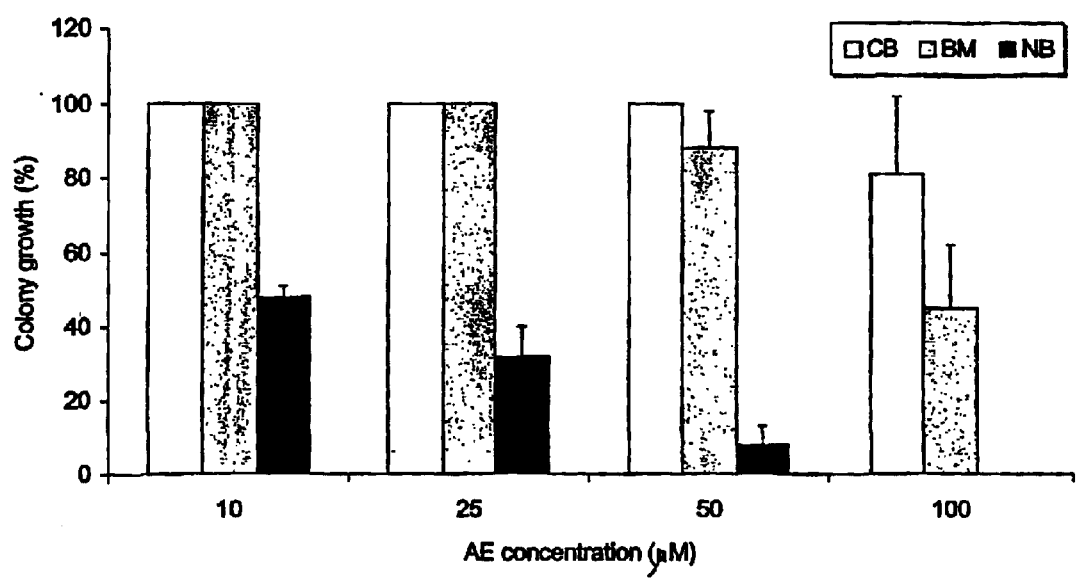

Clonogenic tests have also been carried out on hemopoietic progenitors cells, obtained from bone marrow (BM ▦) of healthy donors and from cord blood (CB □), and on neuroblastoma cells (SJ-N-KP ■). The cell have been grown in methyl cellulose with scalar doses of AE in concentrations between 1 and 100 $\mu$M for 14 days. The obtained data indicate ED50 values for the growth of CFU-GM colonies (colony forming unit-granulocyte/macrophage) varying from 80 and 120 $\mu$M, for hemopoietic cells from bone marrow and from cord blood respectively, whereas the colony-forming activity of neuroblastoma cells (NB ■) is inhibited at lower concentrations of AE (FIG. 1C).

In Vivo Bioassays

In vivo tests of toxicity and effectiveness have been carried out on Swiss mice and on mice with severe combined immunodeficiency (SCID) so as to verify the profile of general toxicity and anti-tumor activity.

In the first case assays on acute and chronic toxicity are carried out on Swiss mice (males aged 8–10 weeks) to show possible effects of general toxicity due to AE on weight, neurological and intestinal functions, and hematological parameters. The animals were treated with high doses by intraperitoneal route, between 30 mg/Kg/die and 50 mg/Kg/die, in one administration and with low doses, between 1 mg/Kg/die and 10 mg/Kg/die, for repeated dosages.

The animals were monitored to check possible neurological damages by means of periodically repeated behavioral tests, to check hematic toxicity by means of weekly hemochrome analyses, and to check intestinal toxicity by means of daily faeces analyses. Moreover, the animals have also been weighed twice a week during the whole test. At the end of the tests the animals have been killed and the autopsy has been conducted.

No toxicity has been registered during the tests and the autopsy has not shown any damage to the main organs.

After the toxicity assay, for the second aim assays on anti-tumor effectiveness have been carried out in SCID mice.

The animals (females aged 6–8 weeks) have been inoculated subcutaneously, between the scapulae, with a suspension of neuroblastoma IMR5 or colon adenocarcinoma cells LoVo 109 ($10 \times 10^6$) and have then been treated with 50 mg/kg/die i.p. of AE (○) in DMSO and then diluted in saline solution, whereas control animals (♦) have been treated with DMSO in saline solution by intraperitoneal route. Drug treatment has been repeated for 5 days for a total of 5 doses in both cases.

Figure 2A:
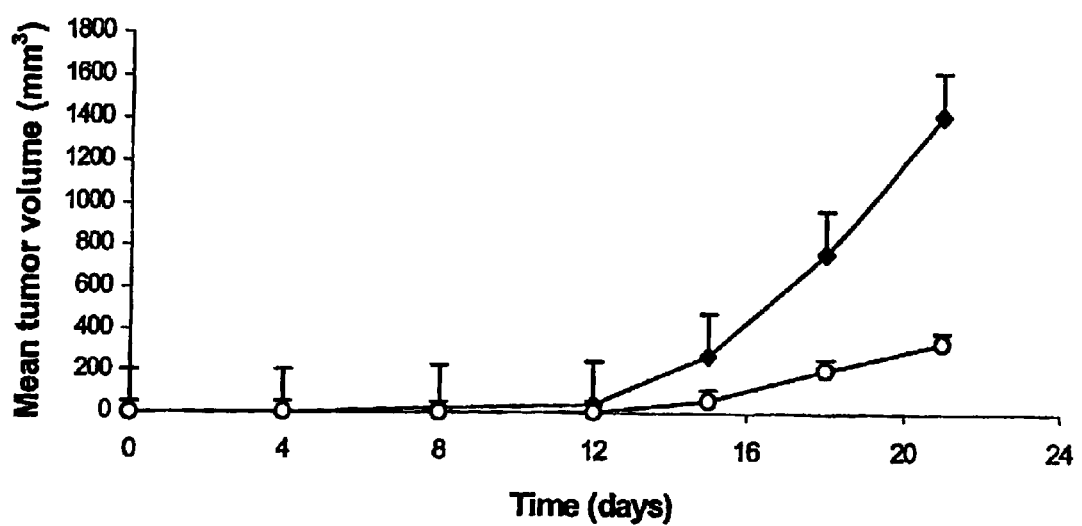
FIG. 2 illustrates antitumor activity of AE in SCID mice carrying human neuroblastoma cells (IMR5 ○) and colon adenocarcinoma cells (LoVo 109 ○) in comparison with a control group treated with vehicule (◆): a) SCID mice injected s.c. with neuroblastoma cells and treated immediately after tumor cell injection and for 5 days with AE for a total of 5 doses; b) SCID mice injected s.c. with neuroblastoma cells and treated with AE at day 15 for 5 days for a total of 5 doses; c) SCID mice injected s.c. with colon adenocarcinoma cells and treated immediately after tumor cell injection and for 5 days with AE for a total of 5 doses.
Figure 2B:
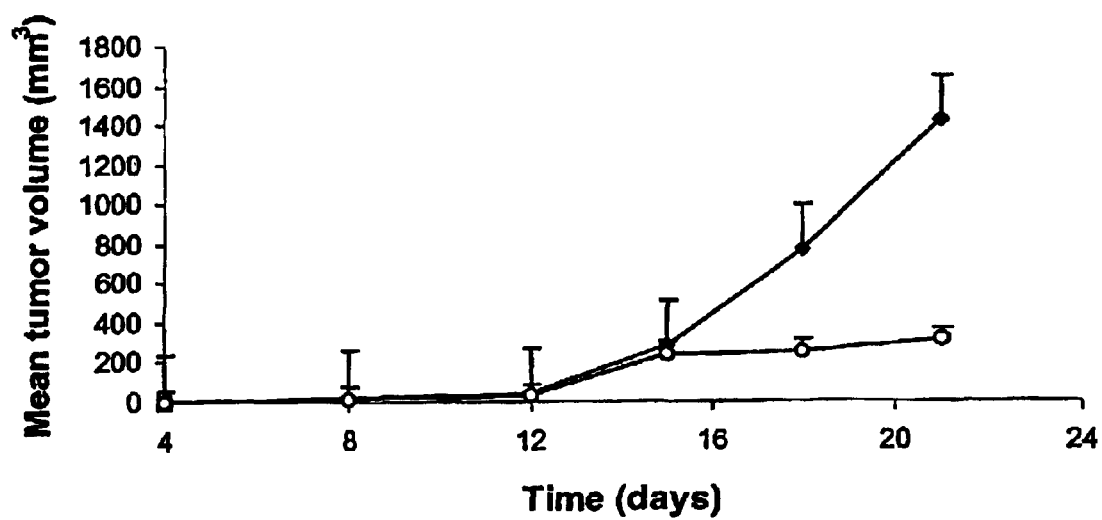
Figure 2C:
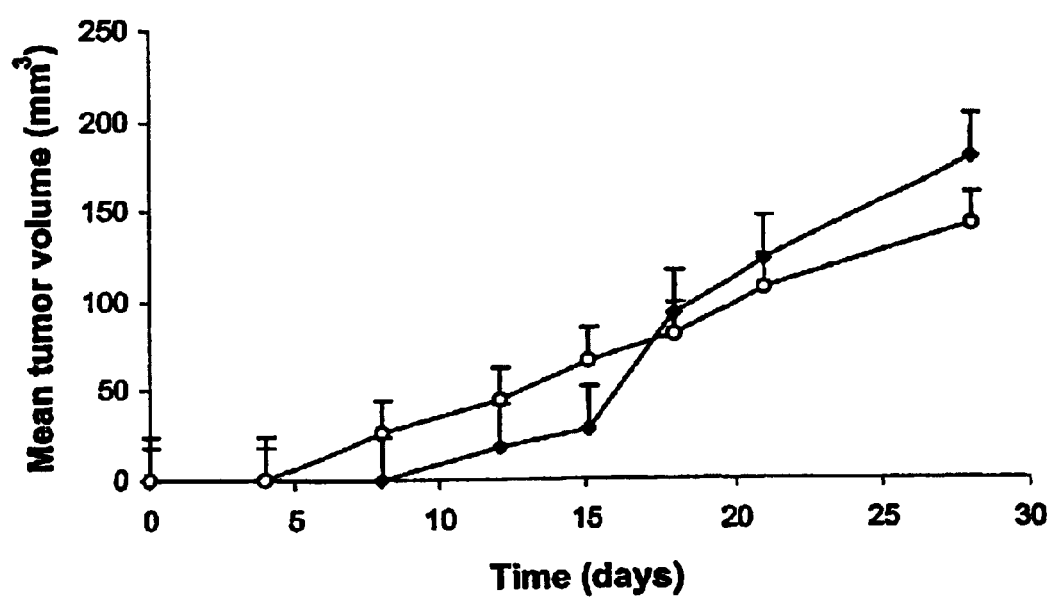

The test schedules provided for the immediate treatment after the inoculation of the tumor or the treatment after the appearance of the tumoral mass (15 days after the tumor cell inoculation). In both cases the mice have been treated for 5 days and then killed when the control mass reached 1.5 cm$^3$. The same tests made on Swiss mice have been carried out and the tumoral masses have been measured with a caliper twice a week. The obtained data on SCID mice show that AE inhibits the appearance of neuroblastoma for 15 days from the inoculation (FIG. 2A) and blocks the growth of the developed mass even when treated at day 15 after tumor cells injection (FIG. 2B) during the period of treatment. On the other side, in the mice inoculated with colon adenocarcinoma the tumor growth does not change after the treatment with AE (FIG. 2C).

The results obtained and briefly described show that free and not glycosylated AE acts as a powerful chemotherapy agent specifically on neuroectodermal tumors. As a matter of fact, it inhibits the growth of human neuroectodermal tumors both during the mass-formation stage and when the mass has already developed.

Moreover, the anti-tumor effect is in no way associated with cytotoxicity process on other dividing normal cells and without relevant toxic effects in animals. The compound does not inhibit in vitro the growth of normal fibroblasts or of human hemopoietic progenitors.

On the contrary, the glycosylated form of AE having formula 10-1,5anhydroglucosyl-1,8-dihydroxy-3-hydroxymethyl-9-anthrone, has no cytotoxic effect on the neuroectodermal tumor cells taken into consideration.

The identified mechanism of cytotoxicity is particularly interesting and new for anti-tumor drugs in general and it consists in the induction of a mechanism of apoptotic cell death, whereas the selectivity against neuroectodermal tumor cells is based on a receptor-mediated cell-specific incorporation of the molecule.

In conclusion, the test results clearly show that the compound taken into consideration can be used as chemotherapeutic agent against neuroectodermal tumors, its advantages being both of having a relevant specific pharmacological effect in vitro and in vivo against these cells and of having no toxic effect in general. Moreover, AE has the further advantage of having no adverse effect on highly important proliferative cells such as hematopoietic progenitors.

Aloe-emodin, therefore, proves to be a suitable eligible compound for the treatment of tumoral pathologies of neuroectodermal origin (such as for instance neuroblastoma, primitive peripheral neuroectodermic tumor (pPNET), Ewing's sarcoma, melanoma and microcytoma etc.), since it has an advantageous potential therapeutic index. This is even more important considering that a neuroectodermal tumor such as neuroblastoma is one of the most common solid tumors in children with an incidence of 10% among all childhood tumors. It should also be observed that during the diagnosis 50% of the children show a clinical picture of metastatic disease with a highly negative prognosis.

It can be used to this purpose in the preparation of pharmaceutical compositions which can be administered to patients in the form of the pharmaceutical compositions which are commonly used for parenteral and oral administration of drugs, as well as in formulations for local administration possibly on the primary and/or secondary site of the tumor. The compound aloe-emodin can also be used to this purpose for the preparation of pharmaceutical compositions suitable for purging operations in the autologous graft of marrow.

To this purpose all pharmaceutically acceptable excipients can be used, including carriers or devices for controlled-release local administration.

The compositions containing AE as active agent for the treatment of neuroectodermal tumors can be in particular formulations having such a dosage of active agent to obtain the desired therapeutic effect according to the aims of the present invention. Said formulations can be prepared according to known methods or to new pharmaceutical technologies, using support materials, excipients, diluents, emulsifiers, watery or oily or polymeric carriers etc., which are acceptable for pharmaceutical use.

The formulations for parenteral administration can be all traditional pharmaceutical forms, such as vials in watery or oily carriers in buffered solutions or solutions containing suitable suspension agents also in the form of lyophilized product to be dispersed before administration.

The formulations for oral administration can be tablets, oily or coated capsules of hard or soft gelatin, pills, dispersible powders, suspensions and emulsions.

The compositions according to the present invention can also consist of formulations for topic or transdermal use in carriers or devices suitable for the administration of the active agent on the primary or secondary tumor site.

Excipients, binding agents, lubricants, disintegrators etc. can be of any kind and anyway suitable for pharmaceutical use and to the purposes of the present invention, such as for instance sugars (for instance mannitol, lactose, dextrose, sucrose, fructose), natural polysaccharides such as cellulose and its derivatives such as methyl cellulose, carboxymethyl cellulose, starches and alginates beyond other known polymeric excipients which are used in the pharmaceutical field, silica, talc, magnesium oxide, stearates, polyethylene glycols, acacia, polyvinyl pyrrolidone and polyvinyl alcohol.

We claim:

1. A method for the treatment of neuroectodermal tumors in a subject which comprises administering to the subject an effective amount of a compound having the formula 1,8-dihydroxy-3-hydroxymethyl-9,10-anthracendione.

2. A method according to claim 1, wherein the neuroectodermal tumors are selected from the group consisting of neuroblastoma, primitive peripheral neuroectodermic tumor, Ewing's sarcoma, melanoma and microcytoma.

3. A method according to claim 1, wherein the compound is administered in a pharmaceutical composition.

4. A method according to claim 3, wherein the pharmaceutical composition is administered by parenteral administration.

5. A method according to claim 4, wherein the parenteral pharmaceutical composition is administered in a form selected from the group consisting of a solution, a suspension, or a lyophilized product to be dispersed before administration.

6. A method according to claim 5, wherein the solution is water-based or oil-based.

7. A method according to claim 3, wherein the pharmaceutical composition is administered by oral administration.

8. A method according to claim 7, wherein the oral pharmaceutical composition is administered in a form selected from the group consisting of a tablet, oily or coated capsules of hard or soft gelatin, pills, dispersible powders, suspensions and emulsions.

9. A method according to claim 3, wherein the pharmaceutical composition is suitable for purging operations in the auto-graft of bone marrow.

10. A method according to claim 3, wherein the pharmaceutical composition is administered by topical or transdermal administration.

11. A method according to claim 10, wherein the topical or transdermal pharmaceutical composition further comprises carriers suitable for the administration of the compound on a primary and/or secondary tumor site.

12. A method according to claim 10, wherein the topical or transdermal pharmaceutical composition is administered in a device suitable for the administration of the compound on a primary and/or secondary tumor site.

* * * * *